(12) United States Patent
Cane' et al.

(10) Patent No.: US 11,684,711 B2
(45) Date of Patent: Jun. 27, 2023

(54) HOUSING FOR A CARTRIDGE FOR DISTRIBUTION AND ADMINISTRATION OF DRUGS BY MEANS OF PORTABLE INFUSION PUMPS

(71) Applicant: CANE' S.P.A., Rivoli (IT)

(72) Inventors: Claudio Cane', Rivoli (IT); Mario Cane', Rivoli (IT); Paolo Cane', Rivoli (IT)

(73) Assignee: CANE' S.P.A., Rivoli (IT)

( * ) Notice: Subject to any disclaimer, the term of this patent is extended or adjusted under 35 U.S.C. 154(b) by 138 days.

(21) Appl. No.: 16/468,786

(22) PCT Filed: Dec. 13, 2017

(86) PCT No.: PCT/IB2017/057899
§ 371 (c)(1),
(2) Date: Jun. 12, 2019

(87) PCT Pub. No.: WO2018/109689
PCT Pub. Date: Jun. 21, 2018

(65) Prior Publication Data
US 2020/0016328 A1    Jan. 16, 2020

(30) Foreign Application Priority Data

Dec. 13, 2016   (EP) ..................................... 16203893

(51) Int. Cl.
*A61M 5/142*   (2006.01)
*A61M 5/145*   (2006.01)

(52) U.S. Cl.
CPC ...... *A61M 5/14244* (2013.01); *A61M 5/1452* (2013.01); *A61M 5/14212* (2013.01); *A61M 2005/14208* (2013.01)

(58) Field of Classification Search
CPC ........ A61M 5/142; A61M 2005/14208; A61M 5/14244; A61M 2005/2411; A61M 5/24; A61M 2005/2403; A61M 2205/10; A61M 5/14212; A61M 5/14248; A61M 5/1452; (Continued)

(56) References Cited

U.S. PATENT DOCUMENTS 1,746,009 A * 2/1930 Mulford ................... A61M 5/34
604/205
2,702,547 A * 2/1955 Glass ................ A61M 5/14546
128/DIG. 1

(Continued)

*Primary Examiner* — Quynh-Nhu H. Vu
(74) *Attorney, Agent, or Firm* — Howson & Howson LLP

(57) ABSTRACT

A Housing for an infusion pump cartridge adapted to enclose a glass vessel having an open proximal end closed by a slidable piston and a distal end provided with a neck is provided. The housing is made of plastic. The proximal end is provided with a pair of bayonet fitting formations integrally formed on the housing and adapted to enable the cartridge to be fastened to an infusion pump and with connection means adapted to be arranged at the distal end of the vessel for connection to an infusion set. The housing consists of a cylindrical base part, which is provided with an inner flange for abutment of the vessel and on which the fitting formations are formed, and a neck part that can be fastened to the base part by means of snap fitting formations for retaining the glass vessel between the base part and the neck part.

14 Claims, 14 Drawing Sheets

(58) Field of Classification Search
CPC .... A61M 5/14546; A61M 2005/14553; A61M 5/3146
See application file for complete search history.

(56) References Cited

U.S. PATENT DOCUMENTS

| | | | | |
|---|---|---|---|---|
| 3,767,085 | A | * | 10/1973 | Cannon ............ B05C 17/00566 604/82 |
| 3,811,441 | A | * | 5/1974 | Sarnoff .................. A61M 5/24 604/201 |
| 5,472,022 | A | * | 12/1995 | Michel .................. A61M 5/24 604/82 |
| 5,688,254 | A | * | 11/1997 | Lopez ................... A61M 39/14 604/905 |
| 5,693,027 | A | * | 12/1997 | Hansen .................. A61M 5/24 604/232 |
| 5,779,675 | A | * | 7/1998 | Reilly .............. B05C 17/00596 600/432 |
| 5,865,805 | A | * | 2/1999 | Ziemba ............ A61M 5/14546 604/218 |
| 5,925,032 | A | * | 7/1999 | Clements ................ A61M 5/34 606/1 |
| 6,132,414 | A | * | 10/2000 | Herbst .................... A61M 5/20 604/403 |
| 6,447,487 | B1 | | 9/2002 | Cane' |
| D565,176 | S | | 3/2008 | Cane' |
| 7,563,249 | B2 | * | 7/2009 | Schriver ............ A61M 5/14546 604/152 |
| 7,976,514 | B2 | * | 7/2011 | Abry ................... A61M 5/326 604/218 |
| D659,234 | S | * | 5/2012 | Cane ................. A61M 5/14546 D24/108 |
| 8,172,814 | B2 | | 5/2012 | Cane' |
| 9,220,835 | B2 | | 12/2015 | Cane' |
| 9,289,549 | B2 | | 3/2016 | Cane' |
| 9,463,271 | B2 | | 10/2016 | Cane' |
| 9,731,085 | B2 | * | 8/2017 | Osman ................ A61M 5/5086 |
| 2004/0254533 | A1 | * | 12/2004 | Schriver ............ A61M 5/14546 604/131 |
| 2007/0100294 | A1 | * | 5/2007 | Sugita ................ A61M 5/3129 604/263 |
| 2010/0241103 | A1 | * | 9/2010 | Kraft .................... A61M 5/162 604/151 |
| 2013/0204187 | A1 | * | 8/2013 | Avery .................... A61M 5/24 604/111 |
| 2017/0216524 | A1 | * | 8/2017 | Haider .................... G16H 20/13 |
| 2017/0340810 | A1 | | 11/2017 | Cane' et al. |

\* cited by examiner

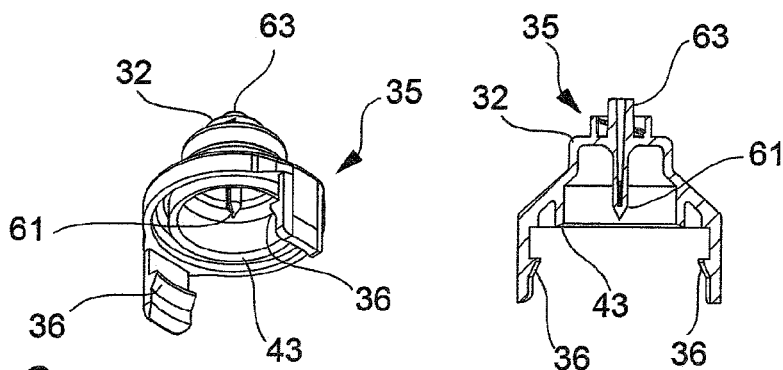
FIG.8a   FIG.8b
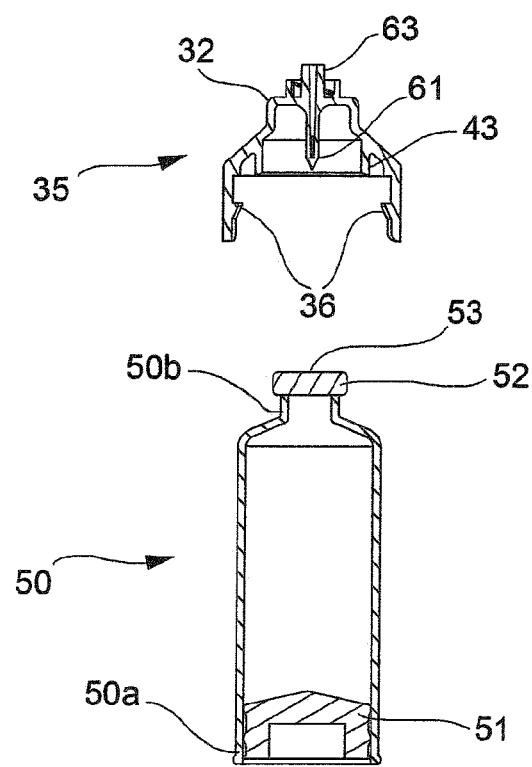
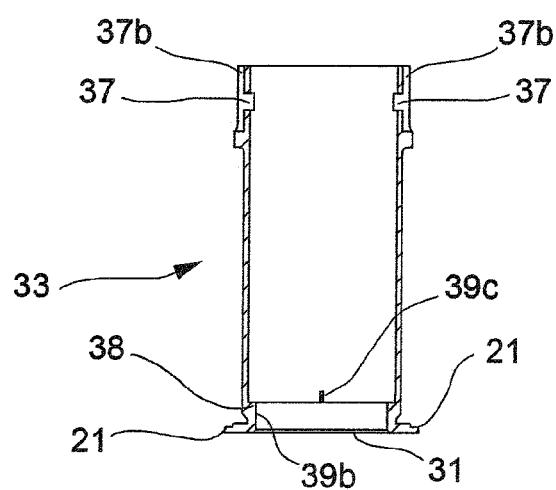
FIG.8c

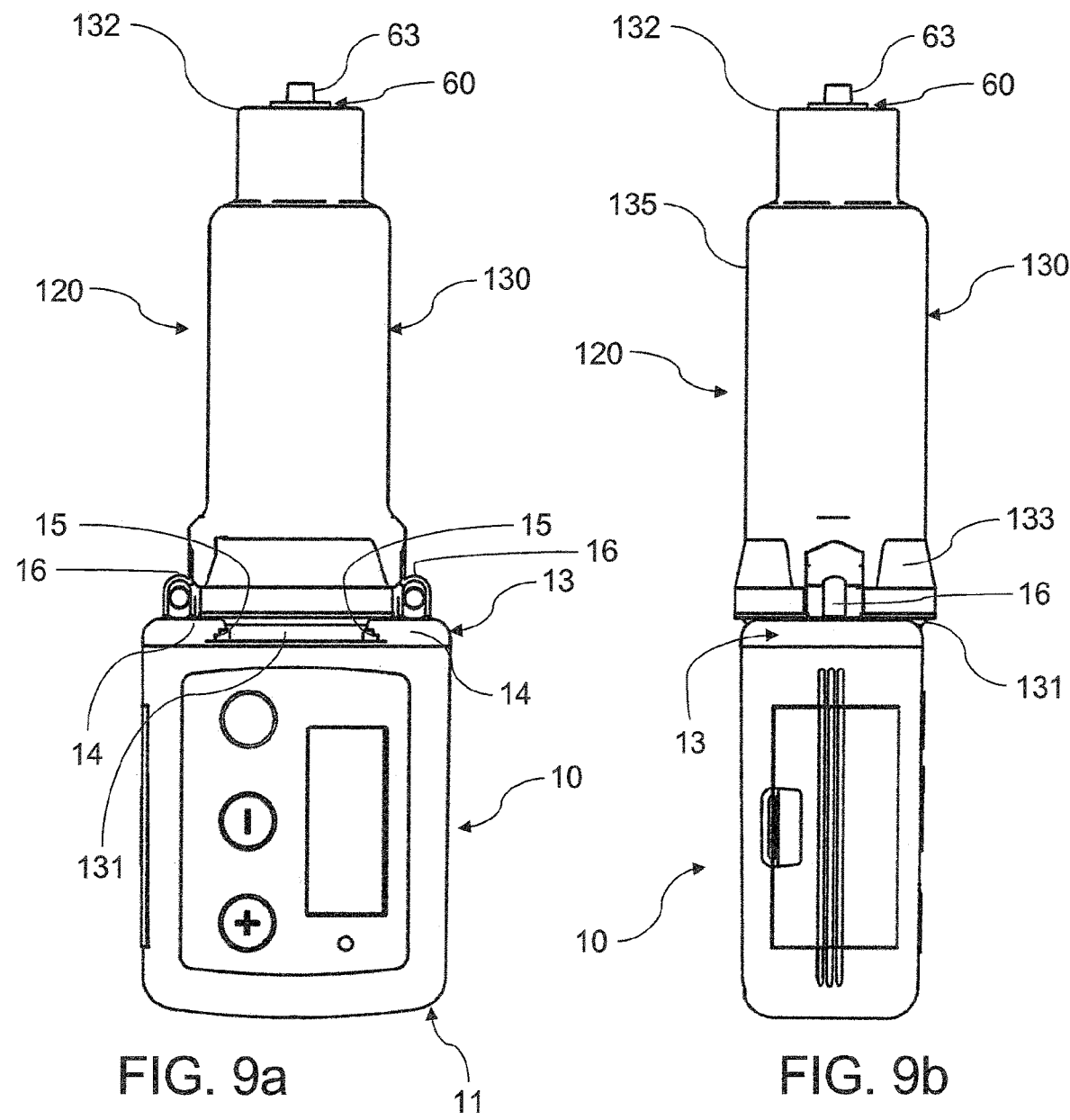

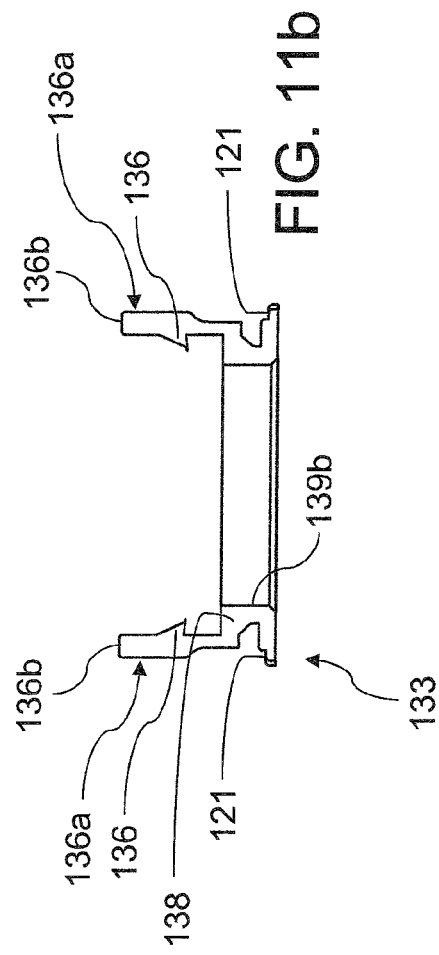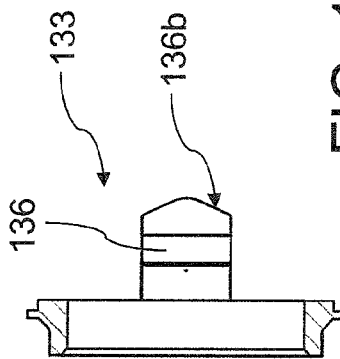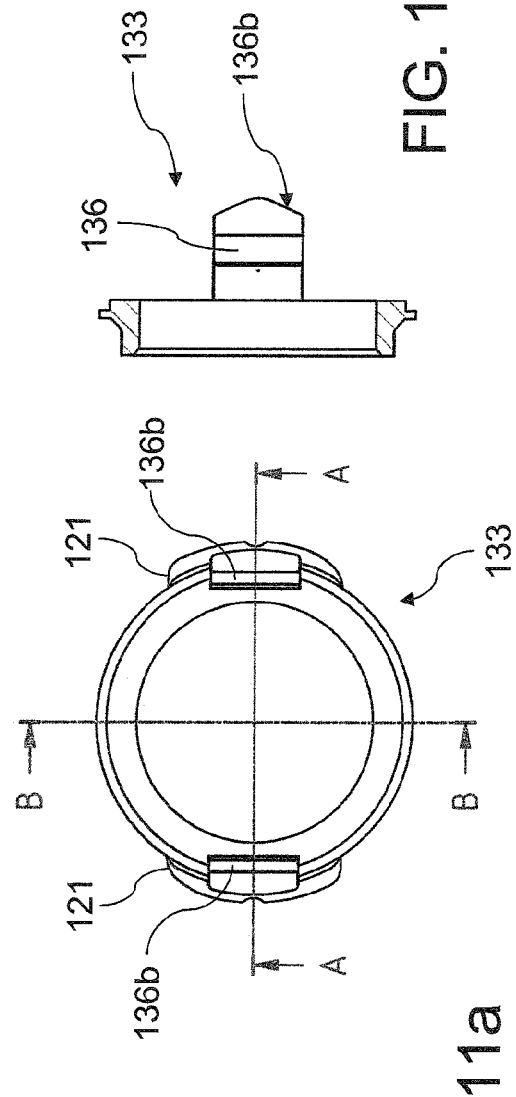

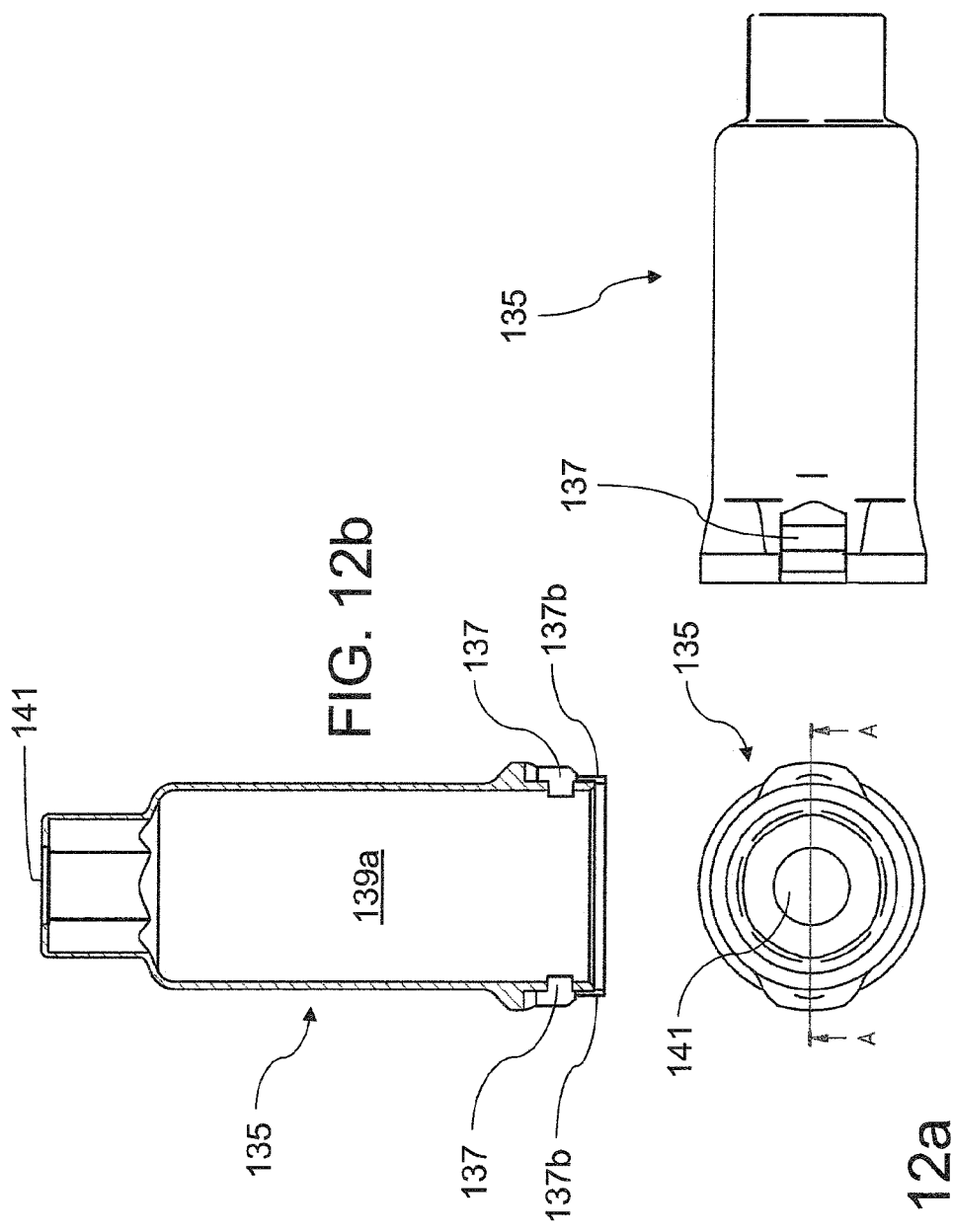

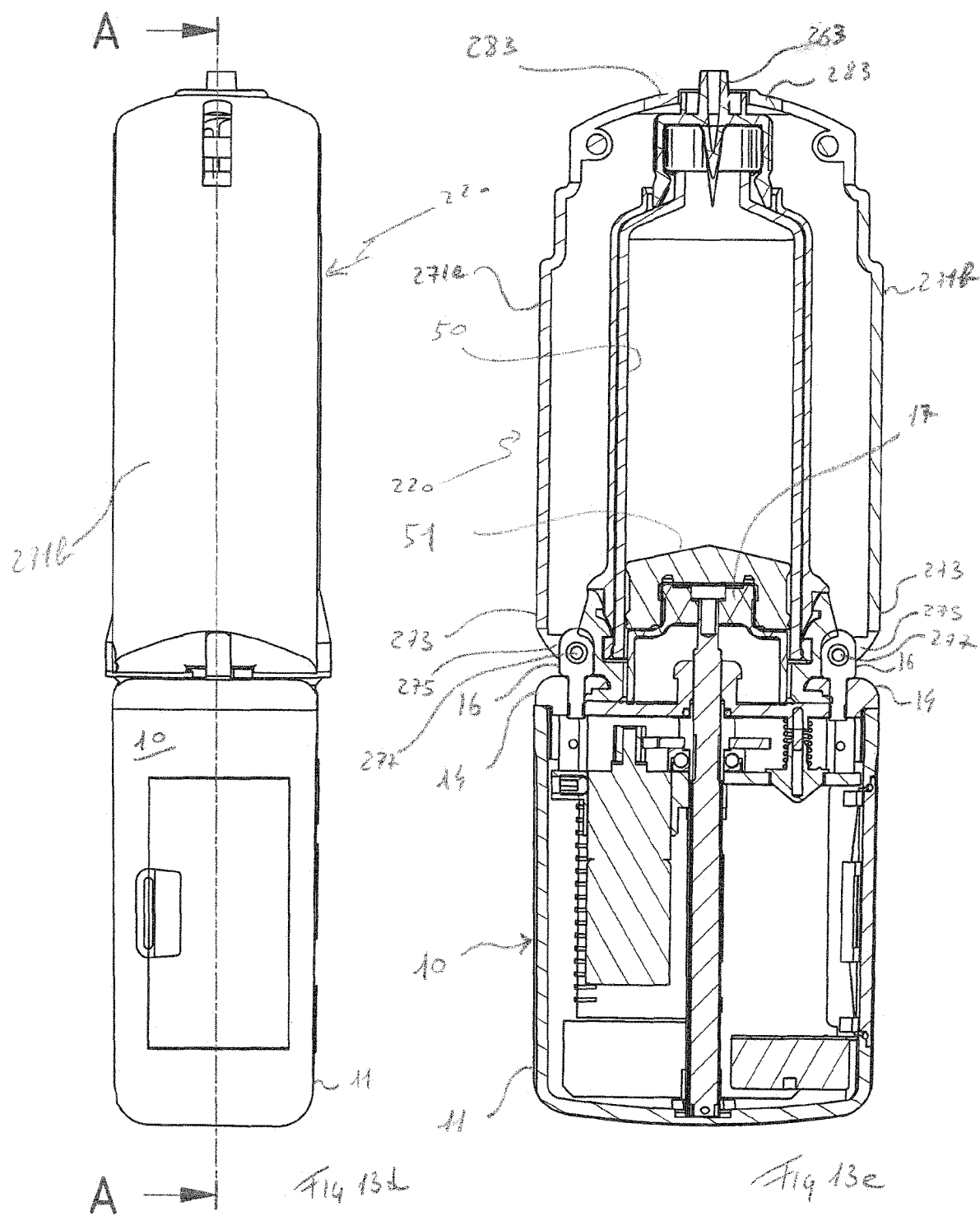

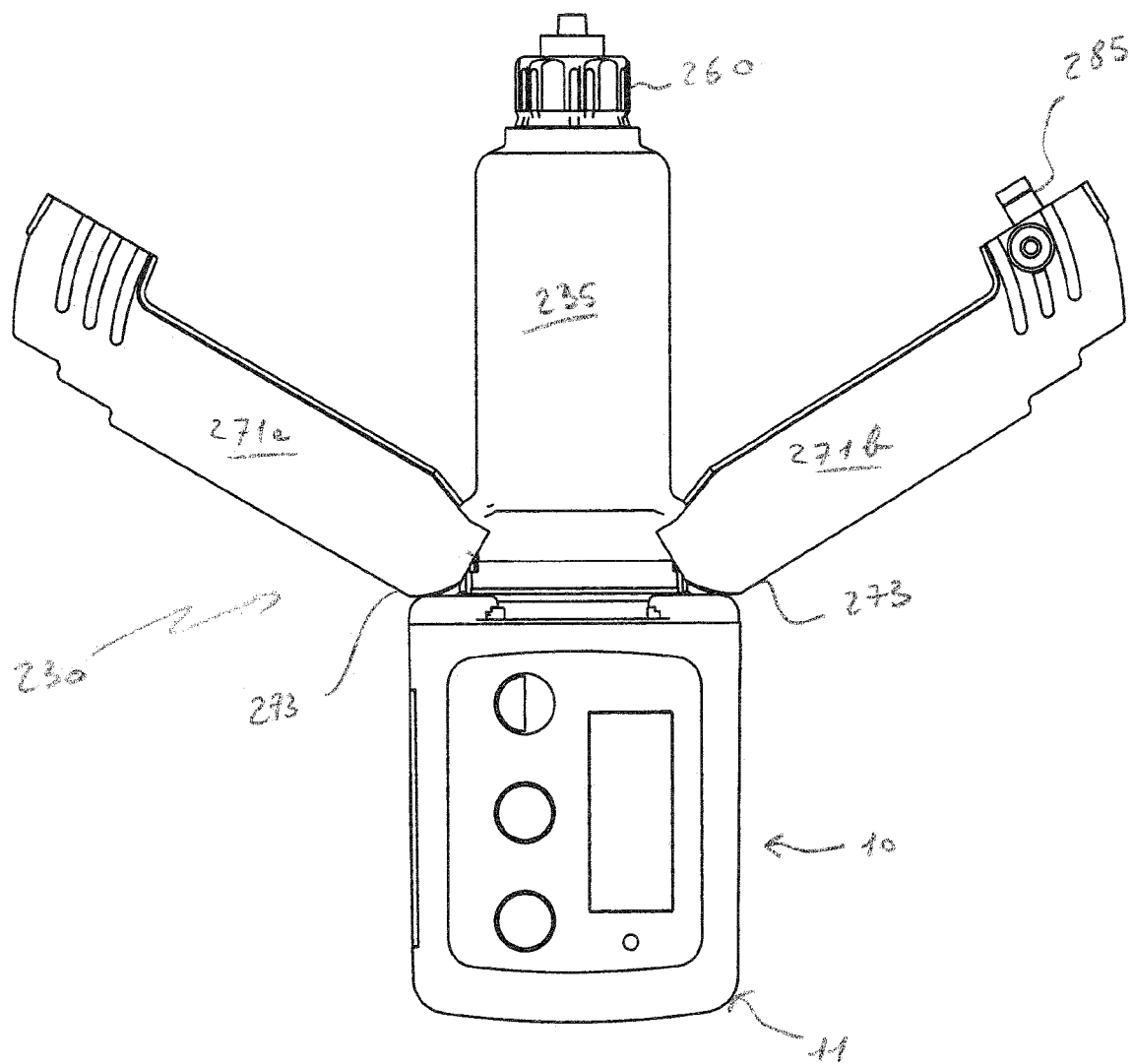

HOUSING FOR A CARTRIDGE FOR DISTRIBUTION AND ADMINISTRATION OF DRUGS BY MEANS OF PORTABLE INFUSION PUMPS

TECHNICAL FIELD

The present invention generally relates to portable infusion pumps for controlled administration of drugs to the human or animal body.

Such infusion pumps serve for injecting drugs in predetermined doses into the patient bearing the device over a predetermined time period, strictly and automatically controlled by the same infusion pump, the pump usually injecting the drug through a tube equipped with an end needle or needle-cannula stably inserted into the human or animal body.

PRIOR ART

Automatically operated portable infusion pumps are known and widely used in the medical field, for instance for controlled administration of insulin to diabetic patients or of various other kinds of drugs in treatment of Parkinson's disease, in ferrochelating therapies or in pain therapy, and other diseases.

The prior art infusion pumps include a pusher that is axially displaceable under the control of a controlled forwarding mechanism and that pushes onto the piston of a cartridge, which contains the dose of drug to be injected and which is removably inserted in a housing provided in the device.

More particularly, in some of the infusion pumps of the kind specified above, the cartridge containing the drug is frontally arranged on the pump body and is equipped with formations engaging in bayonet-like manner with a corresponding frontal seat in the same body through a bayonet coupling. In this case, the cartridge is equipped with a piston having a removable shaft that is used for sucking the drug and is then removed in order to enable the pump pusher, coaxial with the cartridge, to directly act on said piston. More particularly, known devices of this kind are the pumps of the Crono® series produced and commercialised by the Applicant.

Various systems have been proposed to facilitate pouring off the drugs, which generally are kept in vials or other glass vessels, into the infusion cartridges that generally are made of plastic material.

Although such systems enable also persons having no nursing skills to carry out the pouring off operations, the need is felt to further simplify use of infusion pumps.

In this respect, in Italian Patent No. 1331897 in the name of the same Applicant there has been proposed a cartridge including a cylindrical glass vessel having an open proximal end closed by a slidable piston and a distal end provided with a neck having an opening closed by a pierceable membrane, and a housing of plastic material that encloses the vessel and is provided with a pair of bayonet fitting formations that are integrally formed on the housing and are adapted to enable the cartridge to be fastened to the infusion pump. The cartridge further includes a connection system arranged at the distal end of the vessel and intended for connection to an infusion set.

According to such a prior art solution, the cartridge forms a preassembled unit, ready for being used by the patient, who only is to assemble the cartridge on the infusion pump.

Yet, such a prior art solution has a drawback in that it can be unsuitable to fit into the seat provided in the commercially available infusion pumps. Indeed, for a given internal diameter useful for containing the drug, the external size of the cartridge disclosed in Patent No. 1331897 is decidedly greater than that of a simple cartridge of plastics: thus, it may happen that the first cartridge cannot be applied onto a pump for which the second cartridge was on the contrary suited. This is clearly a problem, since use of the cartridge disclosed in Patent No. 1331897 could entail the need to call in the infusion pumps in use and to replace them with other devices suited to the new cartridge.

Therefore, it is an object of the present invention to provide a cartridge for infusion pumps, which is simple to be used by a patient and which does not require any adaptation by the infusion pumps already available on the market.

DESCRIPTION OF THE INVENTION

In view of this object, the invention concerns a housing for a cartridge for an infusion pump for controlled administration of drugs to the human or animal body, said housing being adapted to enclose a glass vessel of cylindrical shape, having an open proximal end closed by a slidable piston and a distal end provided with a neck, wherein said housing is made of plastic material and has a proximal end and a distal end adapted to receive the proximal end and the distal end of the vessel, respectively, wherein the proximal end of the housing is provided with a pair of bayonet fitting formations integrally formed on the housing, and adapted to enable the cartridge to be fastened to an infusion pump, and connection means adapted to be arranged at the distal end of the vessel for fluidically connecting the inside of the vessel with an infusion set, and wherein the housing consists of a cylindrical base part, which is provided with an inner flange for abutment of the vessel and on which the fitting formations are formed, and of a neck part that can be fastened to the base part by means of snap fitting formations for retaining the glass vessel between the base part and the neck part of the housing.

Preferably, the snap fitting formations are configured so as to make separation of the neck part from the base part difficult or substantially impossible, whereby the cartridge and its housing substantially form a disposable assembly.

Use of a cartridge with the housing according to the invention is particularly simple, since no pouring off from a glass vessel is required, but the vessel with the drug is directly used inside a cartridge that can be easily assembled by the patient, since it consists of few elements that can be coupled together with simple operations. In the alternative, in some circumstances, it is possible that the cartridge is delivered to the user in pre-assembled condition: indeed, thanks to the simplicity of the connections among its elements, the cartridge is also suitable for being assembled at industrial level, even in automatic way.

On the other hand, the housing according to the invention, at its portion intended for coupling with the infusion pump, may have external size comparable with the size of the housings of conventional cartridges (i.e. without glass vessel), since it is not required that the glass vessel is to be introduced through the opening at the proximal end of the plastic housing, as it was on the contrary the case for the cartridge disclosed in Italian Patent No. 1331897. Indeed, in the cartridge housing according to the invention, insertion of the vessel into the housing takes place through the opening provided at the distal end of the base part of the housing, before the neck part is assembled: Consequently, it is not necessary that the opening at the proximal end of the housing is so wide as it would be on the contrary required if the vessel ought to be inserted therethrough. In this manner it is possible to keep limited the size of the plastic housing in its part intended for coupling with the infusion pump, so that such size does not exceed the size of the conventional cartridges without glass vessel.

Preferred embodiments of the invention are defined in the dependent claims, which are to be intended as integral part of the present description.

LIST OF THE FIGURES

Further features and advantages of the cartridge according to the invention will become more apparent from the following description of an embodiment of the invention, made with reference to the accompanying drawings, which are given merely for illustrative and non-limiting purposes and in which.

Figure 1:
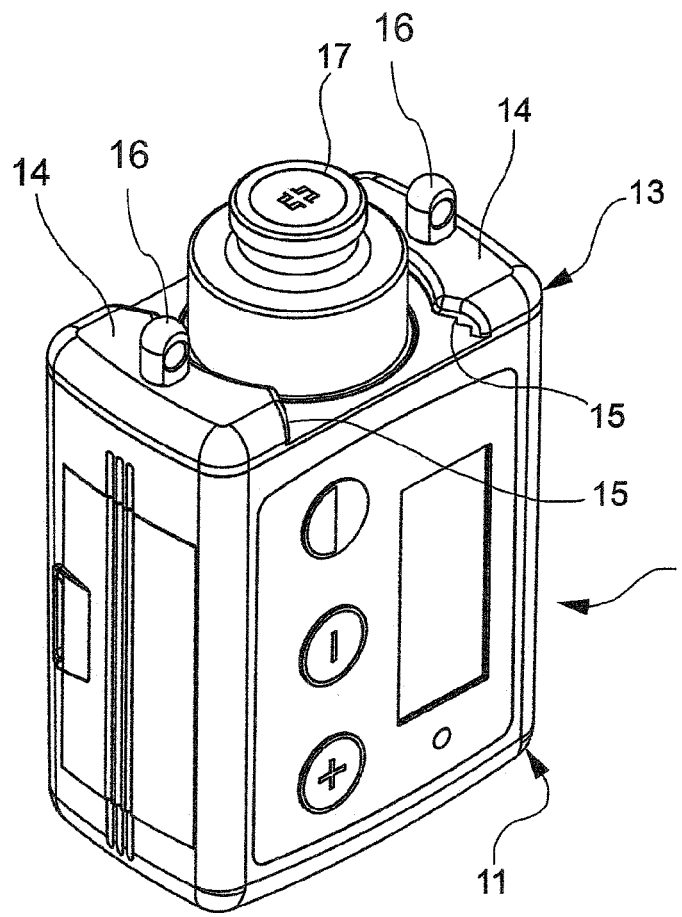
FIG. 1 is a perspective view showing a prior art infusion pump onto which a cartridge with a housing according to the invention can be mounted.
Figure 4:
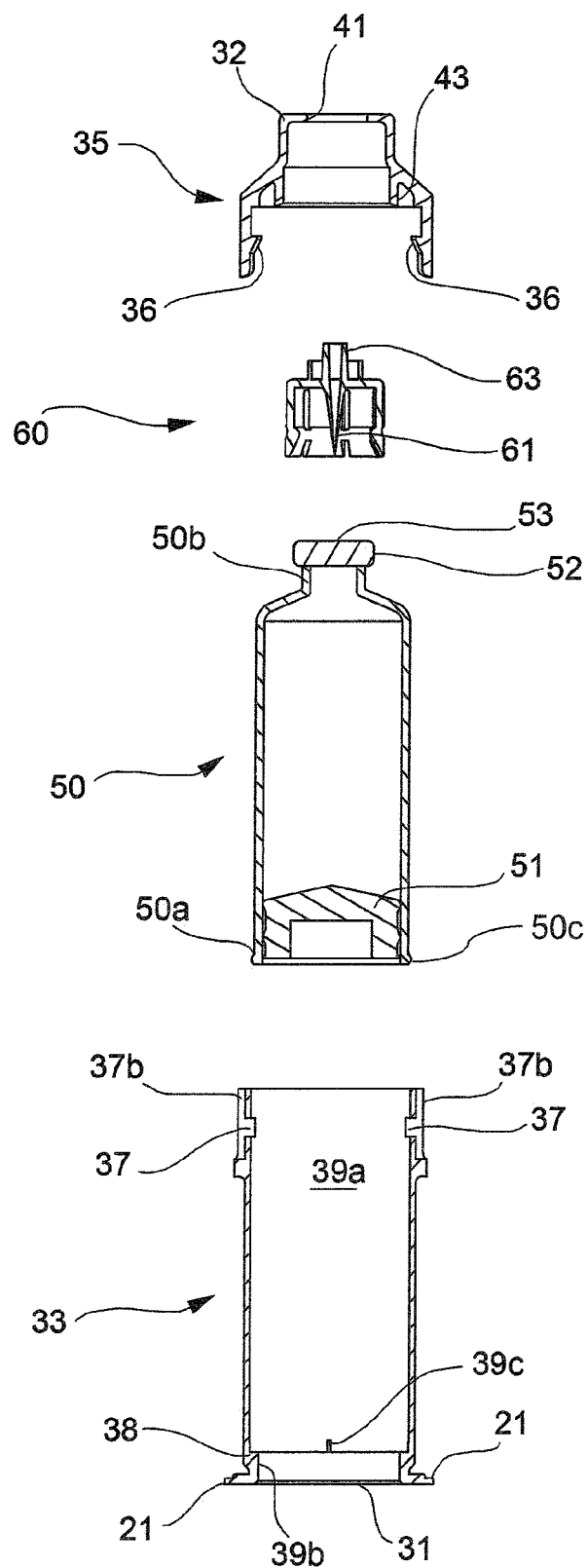
FIG. 4 is an exploded view of the cartridge with the housing in accordance with the first embodiment of the invention.
Figure 6:
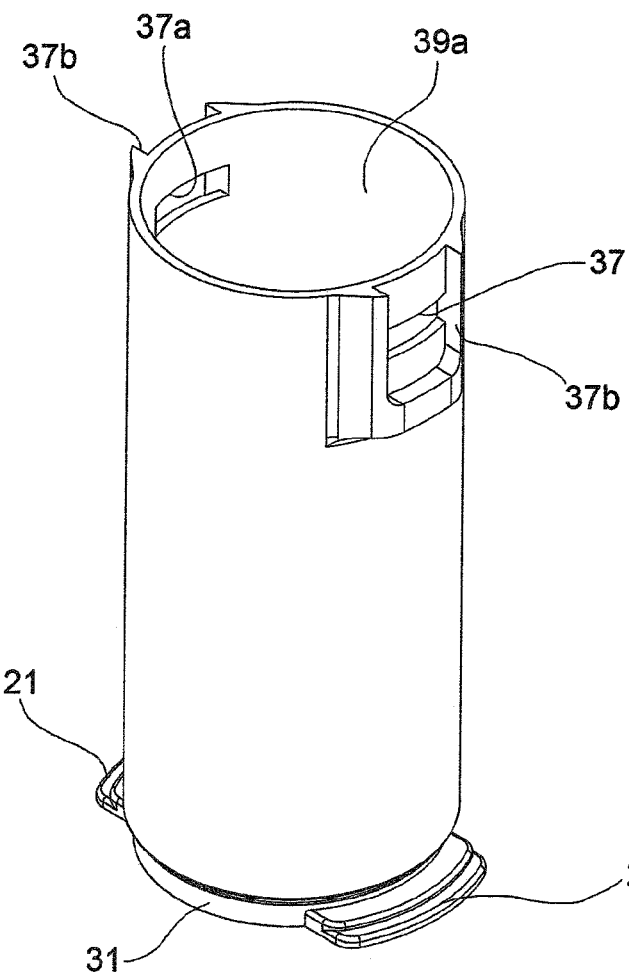
FIG. 6 is a perspective view of a base part of the housing of the cartridge shown in FIG. 4.
Figures 7A, 7B:
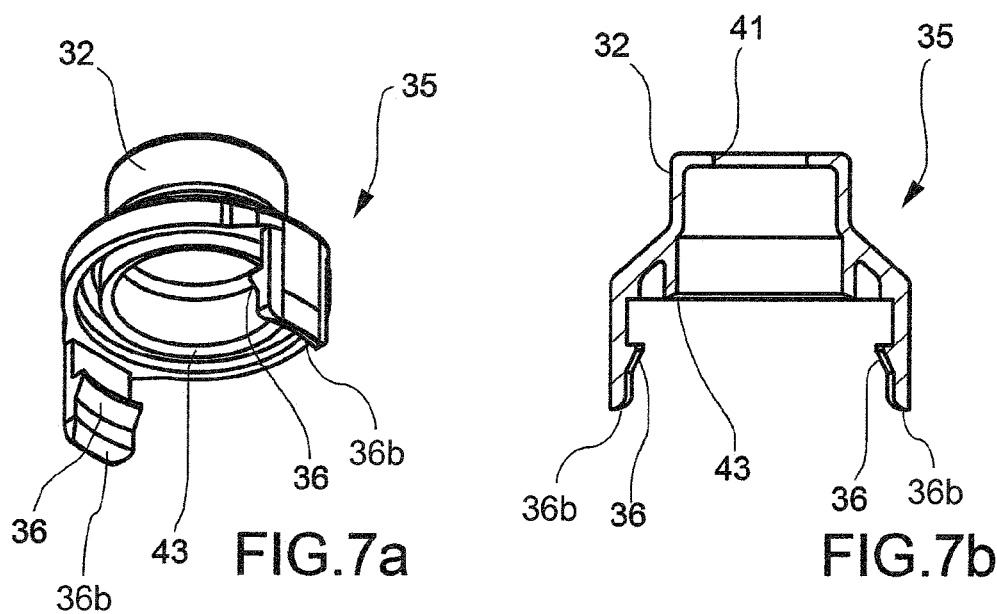
Figure 10B:
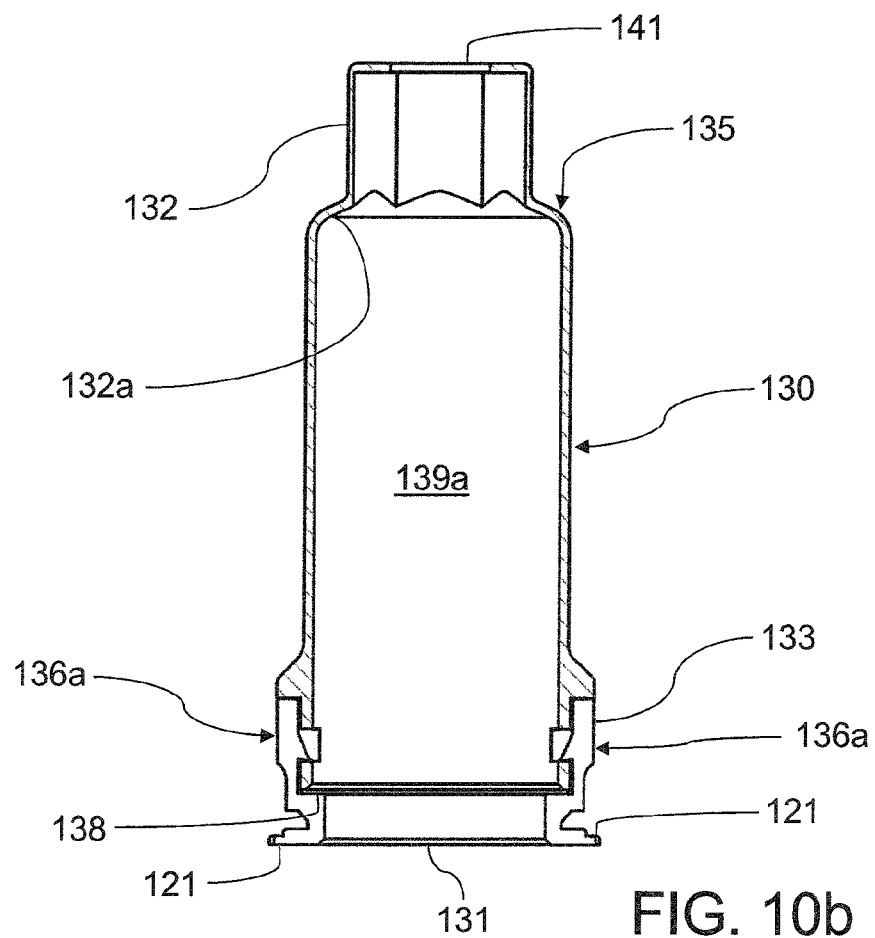
Figure 10A:
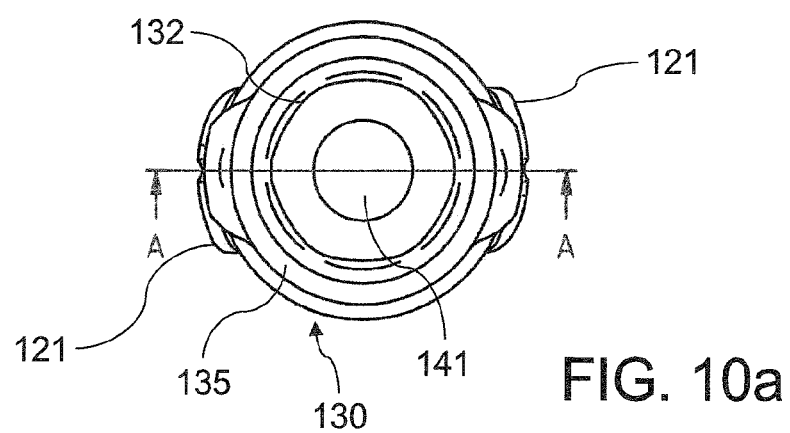

FIGS. 7*a* and 7*b* are a perspective and a sectional view, respectively, of a neck part of the housing of the cartridge shown in FIG. 4;

FIGS. 8*a* and 8*b* are a perspective and a sectional view, respectively, of a neck part of the housing in accordance with a second embodiment of the housing according to the invention;

FIG. 8*c* is an exploded view of the cartridge of the second embodiment;

FIG. 9*a* is a front elevational view showing the infusion pump of FIG. 1 on which a cartridge with a housing in accordance with a third embodiment of the invention is inserted;

FIG. 9*b* is a side elevational view showing the infusion pump of FIG. 1 on which a cartridge with a housing in accordance with a third embodiment of the invention is inserted;

FIG. 9*c* is a top elevational view showing the infusion pump of FIG. 1 on which a cartridge with a housing in accordance with the third embodiment of the invention is inserted;

FIG. 10*a* is a top elevational view of the housing in accordance with the third embodiment of the invention;

FIG. 10*b* is a longitudinal sectional view taken along plane A-A in FIG. 10*a;*

FIG. 11*a* is a top elevational view of the base part of the housing shown in FIG. 10;

FIG. 11*b* is a longitudinal sectional view taken along plane A-A in FIG. 11*a;*

FIG. 11*c* is a longitudinal sectional view taken along plane B-B in FIG. 11*a;*

FIG. 12*a* is a top elevational view of the neck part of the housing shown in FIG. 10;

FIG. 12*b* is a longitudinal sectional view taken along plane A-A in FIG. 12*a;*

FIG. 12*c* is a front elevational view of the neck part of the housing shown in FIG. 12*a;*

Figure 13A:
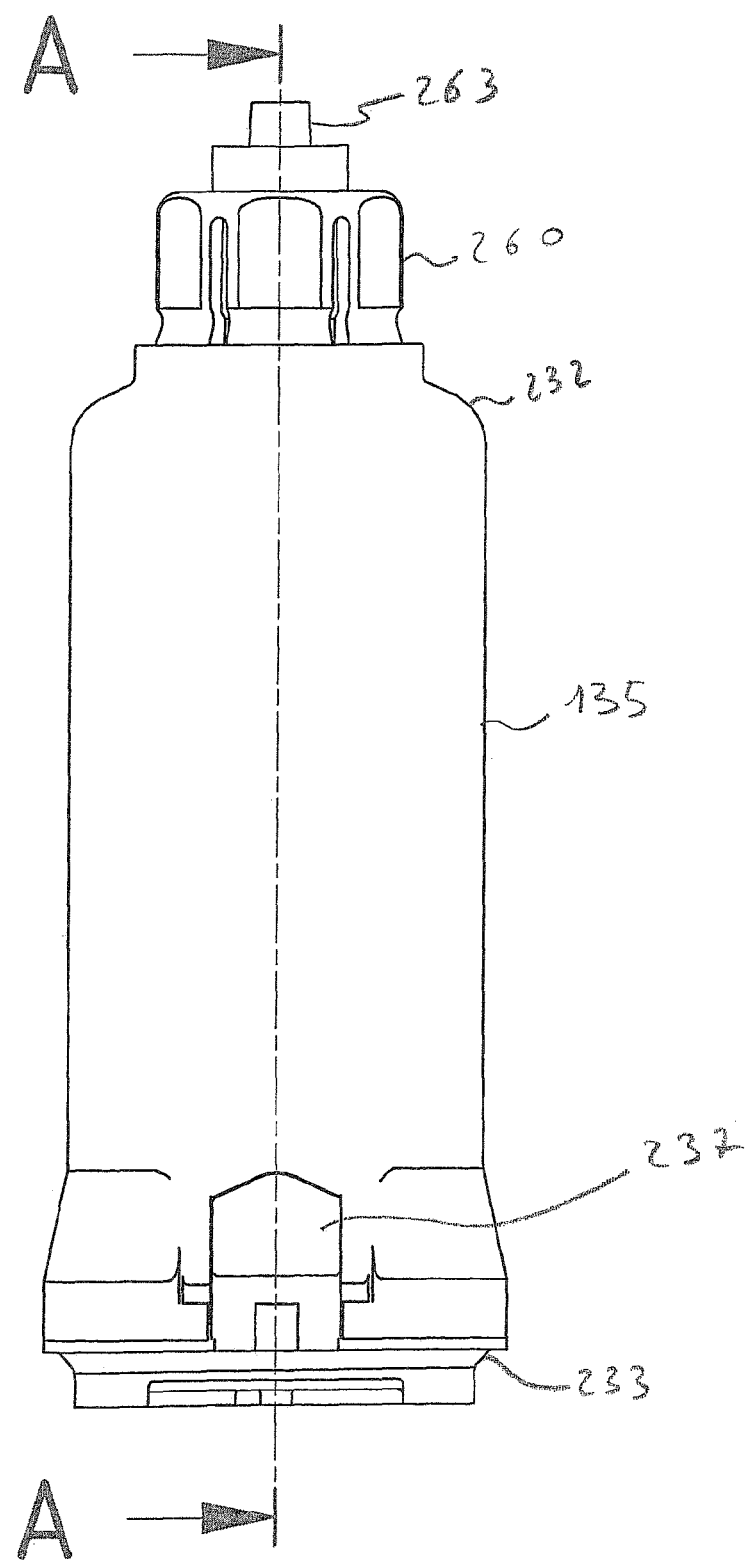
Figure 13B:
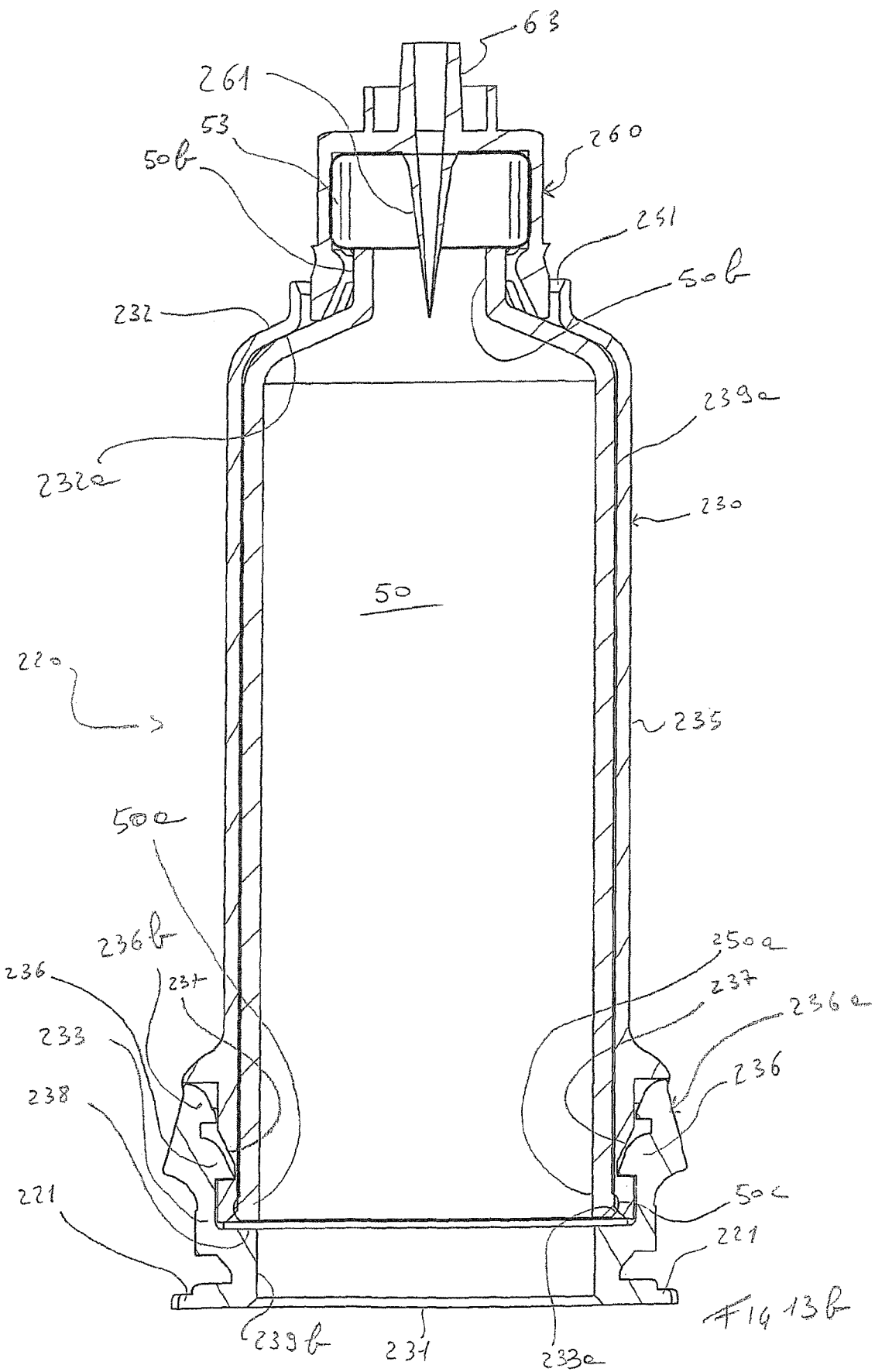

FIG. 13*a* is an elevational view showing a cartridge with a housing in accordance with a fourth embodiment of the invention;

FIG. 13*b* is a longitudinal section along plane A-A- of FIG. 13*a;*

Figure 13C:
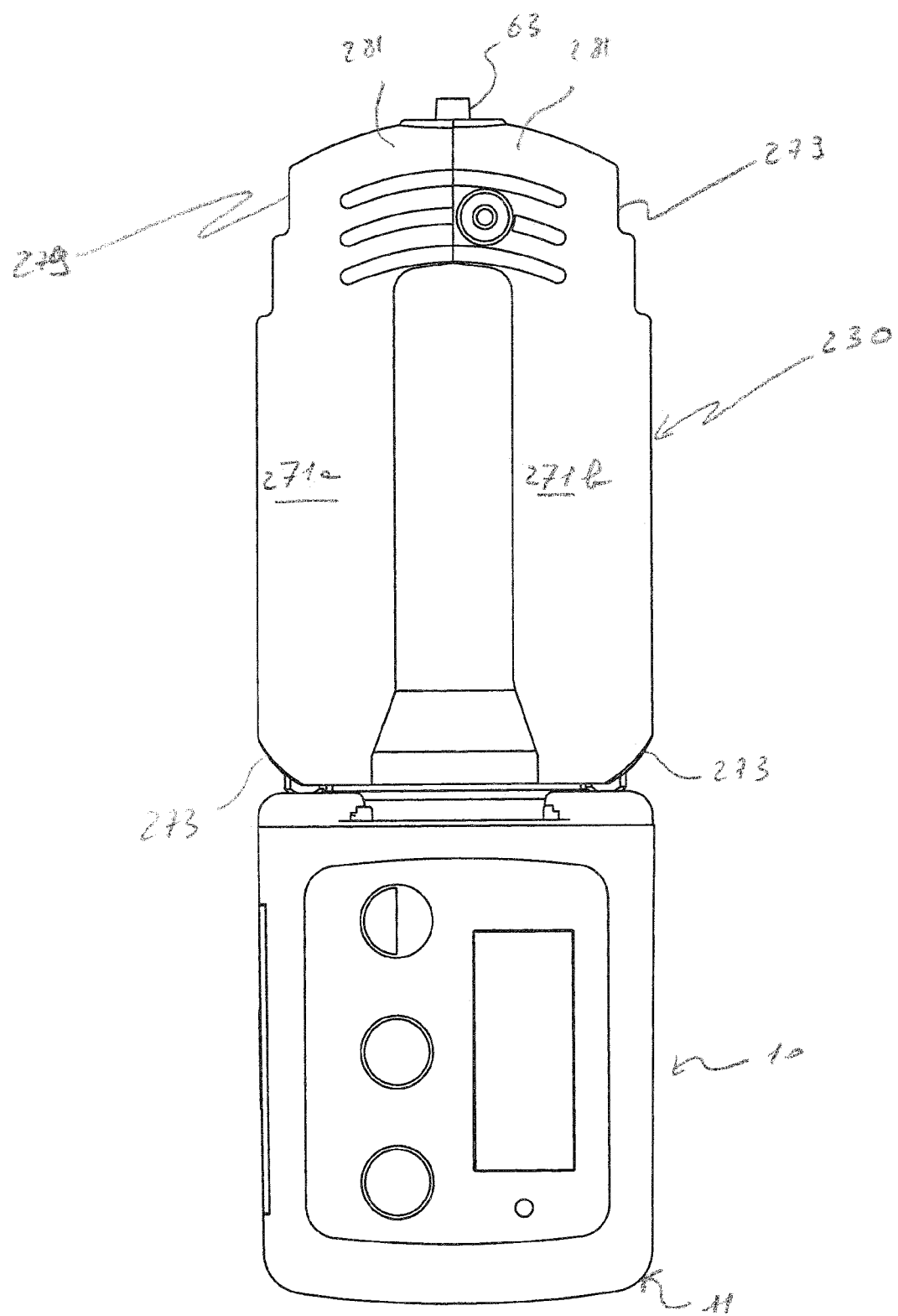

FIG. 13*c* is an elevational view showing the cartridge of FIG. 13*a* mounted on the infusion pump of FIG. 1, with closed wings;

FIG. 13*d* is a side elevational view showing the cartridge of FIG. 13*a* mounted on the infusion pump of FIG. 1;

FIG. 13 *e* is a sectional view along plane A-A of FIG. 13*d;*

FIG. 13*f* is an elevational view showing the cartridge of FIG. 13*a* mounted on the pump of FIG. 1, with open wings.

In all Figures, the same reference numerals have been used to denote equal or functionally equivalent components.

DESCRIPTION OF SOME PREFERRED EMBODIMENTS

Figure 2:
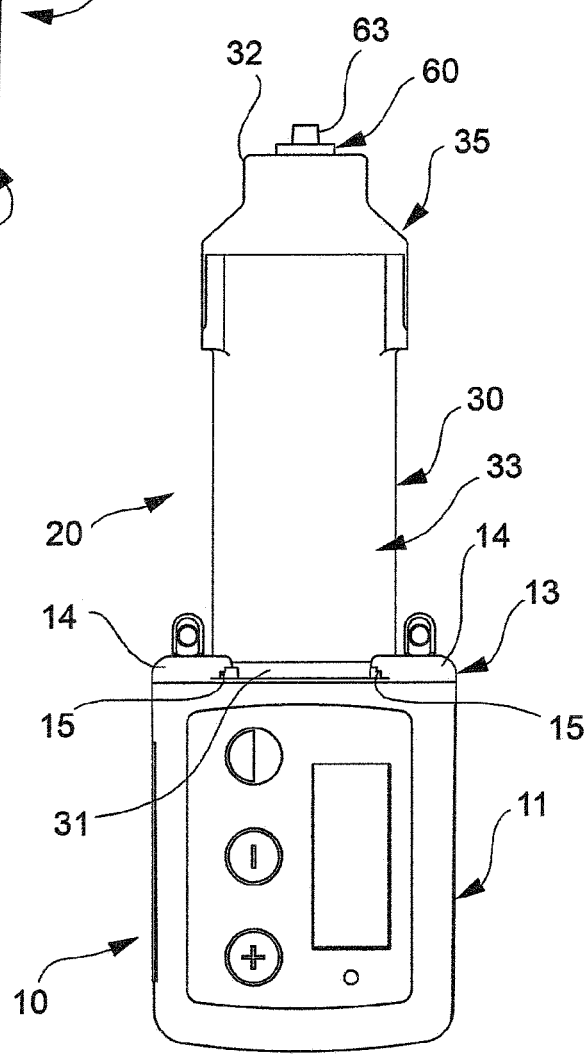
FIG. 2 is an elevational view showing the infusion pump of FIG. 1 on which a cartridge with a housing in accordance with a first embodiment of the invention is inserted.
Figure 3:
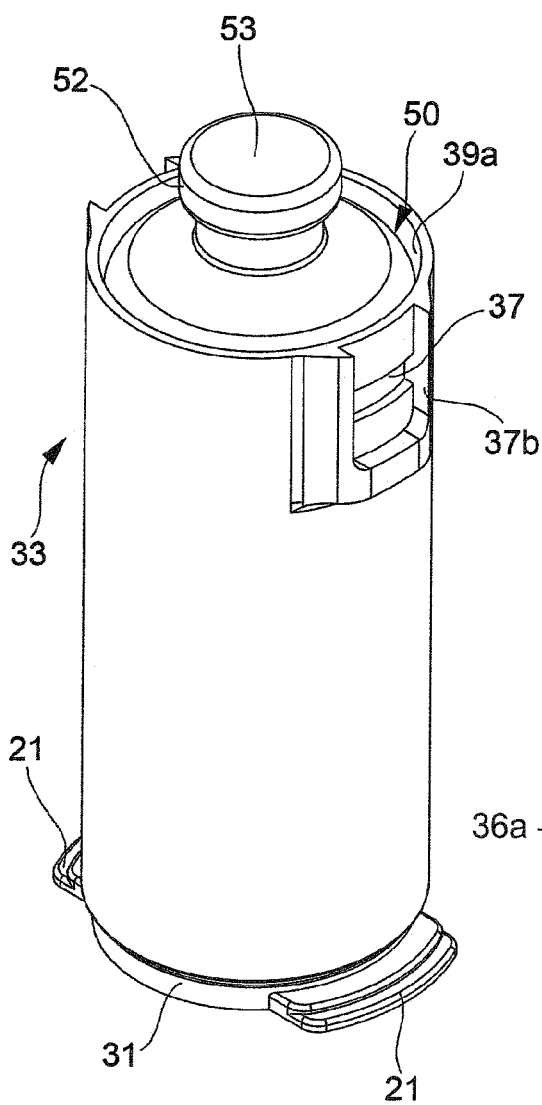
FIG. 3 is a perspective view showing part of a cartridge with a housing in accordance with the first embodiment of the invention.
Figure 5:
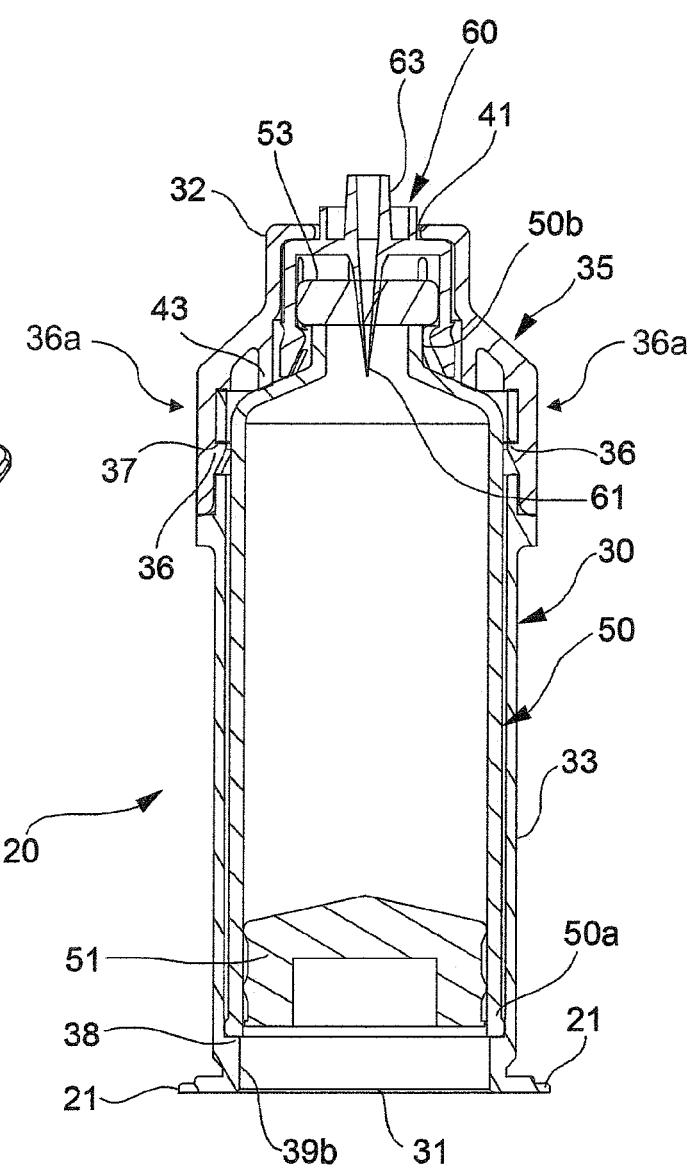
FIG. 5 is a longitudinal sectional view of the cartridge shown in FIG. 4.

Referring to FIGS. 1 and 2, there is shown an infusion pump 10, of a type known per se, for controlled administration of drugs to the human or animal body.

Such a device substantially includes a casing 11 on which a socket 13 is formed for inserting a cartridge. The socket essentially comprises a pair of retaining projections 14, arranged in fork configuration, on which a pair of opposite slits 15, facing the fork inside, are formed. Eyelets 16 are provided on retaining projections 14 surrounding socket 13. Said eyelet 16 are diametrically opposite with respect to the longitudinal axis of the pump passing through the centre of socket 13, and mainly serve for fastening a strap or small chain or the like for suspending the pump, for instance on the bearer's shoulder.

An opening, through which a pusher 17 can extend outwards, is further provided inside the fork. Such a pusher 17 is intended for moving a piston of the cartridge.

For longitudinally moving pusher 17, an electric motor and associated gears are provided in conventional manner, whereas for controlling the electric motor a programmable control unit is provided in conventional manner.

In order to program the control unit depending on the desired therapeutic program, interface devices can be provided, such as a display and/or light and/or sound indicators, as well as keys and/or other data input devices, located on casing 11 of the device.

A particular example of the infusion pump described above is represented by the devices of the Crono® series produced and commercialised by the same Applicant.

FIG. 2 shows pump 10 with a cartridge 20 inserted in socket 13. In order to allow inserting cartridge 20 onto pump 10, the external surface of the cartridge is conventionally provided with a pair of fitting formations or blades 21 enabling axially inserting the cartridge inside the fork of socket 13 and, after the cartridge has been turned by 90° about its longitudinal axis, retaining it in slits 15 of retaining projections 14.

The connection system disclosed above is given by way of example only, other kinds of bayonet coupling being possible. For instance, cartridge configurations with greater capacity are known, where fitting formations 21 are formed on the internal surface of the cartridge, and the slits receiving such fitting formations face away from the fork of socket 13.

Referring to FIGS. 3 to 7, cartridge 20 includes a housing 30 of plastic material having an open proximal end 31 and an open distal end 32 and consisting of a cylindrical base part 33 (shown in particular in the Figure) and a neck part 35 (shown in particular in FIGS. 7a and 7b).

Base part 33 is substantially shaped as a cylindrical cup having a proximal end and a distal end. Neck part 35 is substantially shaped as an inverted funnel with a neck, and it has a proximal end and a distal end. The proximal end of base part 33 coincides with the proximal end of housing 30 itself. The distal end of neck part 35 coincides with the distal end of housing 30. When housing 30 is assembled, the distal end of base part 33 substantially matches the proximal end of neck part 35.

In order to enable the mutual fastening of base part 33 and neck part 35, snap fitting formations are provided, which are integrally formed on the outer surfaces of such parts. In the example illustrated, the snap fitting formations include a pair of diametrically opposite teeth 36 formed on tabs 36a axially extending from neck part 35 of housing 30, and a pair of diametrically opposite seats or openings 37, which are formed on the side wall of base part 33 of housing 30 and into which teeth 36 are inserted when housing 30 is assembled.

In order to make coupling between teeth 36 and seats 37 easier, tabs 36a provided with teeth 36 may be provided with draft end portions 36b with rounded or bevelled edges, and seats 37 may be located within guide grooves 37b.

According to other embodiments, the arrangement of the teeth and the seats may be reversed between the neck and base parts, and the number and the configuration of the elements implementing the snap fitting can be different from those described. Yet, an arrangement is preferred in which the positions of the teeth and the seats are angularly aligned with the positions of bayonet fitting formations 21, so that the size of the assembly in a direction orthogonal to the direction of fitting formations 21 is not increased.

At its proximal end 31, base part 33 of housing 30 has a portion tapered in the proximal direction, the outer diameter of which is reduced with respect to the remaining part of base part 33 and on which fitting formations 21 are formed.

Inside base part 33 of housing 30, a substantially cylindrical cavity 39a is formed, which is defined at the proximal end by an internal flange 38 integrally formed on base part 33 and is located in correspondence of the tapered portion on which fitting formations 21 are formed. Internal flange 38 thus surrounds an opening 39b having smaller diameter than internal cavity 39a of base part 33.

Near internal flange 38, the internal surface of base part 33 can be provided with axial ribs 39c.

At its proximal end, neck part 35 of housing 30 has substantially the same diameter as internal cavity 39a of base part 33. At its distal end 32, neck part 35 has an opening 41 with a smaller diameter than the proximal end.

At a position intermediate the proximal and distal ends of neck part 35 of housing 30, a collar-shaped projection 43, concentrically arranged relative to opening 41, is formed on the internal side of neck part 35.

Cartridge 20 further includes a glass vessel 50 containing a drug and enclosed inside housing 30.

Vessel 50 has a substantially cylindrical shape ending with a neck at a distal end, and has an open proximal end 50a closed by a slidable piston 51 and a distal end 50b with an opening closed by a cover 52 equipped with a pierceable membrane 53.

Cartridge 20 further includes connection means adapted to be arranged at distal end 50b of vessel 50.

In the embodiment shown in FIGS. 3 to 7, such connection means include a connection element 60 secured to distal end 50b of vessel 50, for instance secured to cover 52 as a cap, through integral resilient elements which cling around the edge of said cover. Connection element 60, for instance of the "spike" type, has at a proximal end a piercing element 61 for piercing membrane 53 of vessel 50, and at a distal end a connector 63, for instance a Luer Lock, for connection to an infusion set including for instance a tube and a needle or needle-cannula (not shown). Through piercing element 61 and one or more passageways for fluid formed inside connection element 60, the inside of the vessel is put in communication with the infusion set.

Proximal end 50a of vessel 50 is received within proximal end 31 of housing 30, with piston 51 being arranged coaxially with opening 39b formed on proximal end 31 of base part 33 of housing 30. The proper and quick alignment of piston 51 with opening 39b is ensured by axial ribs 39c formed inside base part 33 of housing 30. Base part 33 is so sized in length as to enclose the whole of the cylindrical portion of vessel 50, or at least most of such portion.

Distal end 50b of vessel 50 is received within distal end 32 of housing 30.

Retention of vessel 50 inside housing 30 is ensured in that collar-shaped projection 43 of the neck part of housing 30 rests on the tapered portion of vessel 50, between the cylindrical portion and the neck thereof, thereby pushing vessel 50 against internal flange 38 of base part 33 of housing 30.

The assembly described above can be inserted onto the pump shown in the Figures, while ensuring that glass vessel 50 is firmly retained onto the pump thanks to plastic housing 30 enclosing it, and that pusher 17 of the device can properly reach piston 51.

In this manner, precise drug doses can be administered in controlled and reliable manner.

The assembly disclosed above is used as a kit consisting of separate elements, which are assembled at the moment of use. In this case, it is possible either to assemble all parts of cartridge 20 and subsequently insert cartridge 20 on pump 10, or it is possible first inserting base part 33 of housing 30 on pump 10, and then assembling the other parts to base part 30 already inserted.

In the alternative, especially in embodiments (not shown) where the vessel is provided with a closing element which is not pierceable but is removable, and where the connection means lack the piercing element, it is possible to conceive that the kit is assembled at industrial level and then delivered to the users in assembled form.

FIGS. 8a to 8c show an alternative embodiment, or second embodiment, of the invention, which differs from the embodiment described above only in that it lacks the connection element, and hence in that the functions of piercing element 61 and connector 63 for connection to the infusion set are integrally provided on neck part 35 of housing 30.

FIGS. 9 to 12 show a third embodiment of the invention, which substantially differs in the arrangement of the teeth and the seats, which is reversed with respect to the embodiments described above, and in the longitudinal extension of the neck part, which is greater than the longitudinal extension of the base part in comparison to the embodiments described above.

Referring more particularly to FIGS. 9a-9c, infusion pump 10 is shown with a cartridge 120 inserted in socket 13. In order to allow inserting cartridge 120 onto pump 10, the external surface of the cartridge is conventionally provided with a pair or blades 121 enabling axially inserting the cartridge inside the fork of socket 13 and, after the cartridge has been turned by 90° about its longitudinal axis, retaining it in slits 15 of retaining projections 14.

The connection system disclosed above is given by way of example only, other kinds of bayonet coupling being possible. For instance, cartridge configurations with greater capacity are known, where fitting formations 121 are formed on the internal surface of the cartridge, and the slits receiving such fitting formations face away from the fork of socket 13.

Referring more particularly to FIGS. 10 to 12, cartridge 120 includes a housing 130 of plastic material having an open proximal end 131 and an open distal end 132 and consisting of a cylindrical base part 133 (shown in particular in FIG. 11) and a neck part 135 (shown in particular in FIG. 12).

Base part 133 is substantially shaped as a cylindrical cup having a proximal end and a distal end. Neck part 135 is substantially shaped as an inverted barrel with a neck, and it has a proximal end and a distal end. The proximal end of base part 133 coincides with the proximal end of housing 130 itself. The distal end of neck part 135 coincides with the distal end of housing 130. When housing 130 is assembled, the distal end of base part 133 substantially matches the proximal end of neck part 135.

In order to enable the mutual fastening of base part 133 and neck part 135, snap fitting formations are provided, which are integrally formed on the outer surfaces of such parts. In the example illustrated, the snap fitting formations include a pair of diametrically opposite teeth 136 formed on tabs 136a axially extending from base part 133 of housing 130, and a pair of diametrically opposite seats or openings 137, which are formed on the side wall of neck part 135 of housing 130 and into which teeth 136 are inserted when housing 130 is assembled.

In order to make coupling between teeth 136 and seats 137 easier, the tabs provided with teeth 136 may be provided with draft end portions 136b with rounded or bevelled edges, and seats 137 may be located within guide grooves 137b.

In accordance with this third embodiment of the invention, tabs 136a are preferably located so that, when cartridge 120 is inserted onto pump 10, said tabs 136a are radially aligned with eyelets 16 provided on retaining projections 14, arranged in fork configuration, of pump 10. Moreover, base part 133 of housing 130 is suitably sized so that said tabs 136a are in contact with eyelets 16. In other words, eyelets 16 define an abutment shoulder for tabs 136a and consequently prevent outward radial movement thereof.

Advantageously, thanks to such an arrangement, eyelets 16 prevent tabs 136a from radially opening outwards, thereby avoiding the risk that neck part 135 becomes released from base part 133 of housing 130, especially when piston 17 of pump 10 exerts the pushing force on piston 51 of vessel 50. When cartridge 120 is inserted onto pump 10 with vessel 50 inside it, consequently neck part 35 cannot be removed from base part 133 thanks to the engagement of teeth 136 with seats 137 and thanks to the fact that tabs 136a provided with teeth 136 cannot open out outwards due to the provision of eyelets 16.

Other configurations will be possible in which eyelets 16 are replaced by corresponding stop members for tabs 136a. For instance, said corresponding stop members could consist of projections integrally formed in retaining projections 14, or of heads of screws for fastening retaining projections 14.

Advantageously, in accordance with a particular embodiment of the invention, each tab 136a can include two or more axially aligned teeth 136 and, on the side wall of neck part 135 of housing 130, there are formed as many seats or openings 137 into which teeth 136 are inserted when housing 130 is assembled. The two or more teeth 136 provided on each tab 136a can also have mutually different sizes, and preferably the teeth size decreases towards the draft end portion 136b.

At its proximal end 131, base part 133 of housing 130 has a portion tapered in proximal direction, the diameter of which is reduced with respect to the remaining part of base part 133 and on which fitting formations 121 are formed.

Inside neck part 135 of housing 130, a substantially cylindrical cavity 139a is formed. At its proximal end, neck part 135 of housing 130 has substantially the same diameter as the distal end of base part 133. At its distal end 132, neck part 135 has an opening 141 with smaller diameter than its proximal end.

Base part 133 of housing 130 is defined at its proximal end by an internal flange 138, integrally formed on base part 133 and located in correspondence of the tapered portion on which fitting formations 21 are formed. Internal flange 138 thus surrounds an opening 139b having a smaller diameter than internal cavity 139a of neck part 135.

Similarly to the previously described embodiments, cartridge 120 of which housing 130 is part further includes a glass vessel 50 containing a drug and enclosed inside housing 30.

Cartridge 120 further includes connection means adapted to be arranged at distal end 50b of vessel 50.

Proximal end 50a of vessel 50 is received within proximal end 131 of housing 130, with piston 51 being arranged coaxially to opening 139b formed on proximal end 131 of base part 133 of housing 130. The proper and quick alignment of piston 51 with opening 139b is possibly ensured by axial ribs formed inside base part 133 of housing 130. Neck part 135 is so sized in length as to enclose the whole of the cylindrical portion of vessel 50, or at least most of such portion.

Distal end 50b of vessel 50 is received within distal end 132 of housing 130.

Retention of vessel 50 inside housing 130 is ensured in that distal end 132 of neck part 135 has a tapered inner wall 132a forming a corresponding abutment surface and resting on the tapered portion of vessel 50, between the cylindrical portion and the neck thereof, thereby pushing vessel 50 against internal flange 138 of base part 133 of housing 130.

In the alternative, a small passageway can be provided between surface 132a and vessel 50, and vessel 50 can be retained in correspondence of base part 133, for instance through the mutual engagement between an annular projection 50c provided at the base of vessel 50 and a corresponding annular seat (not shown) provided in base part 133.

The assembly described above can be inserted onto the pump shown in FIG. 9, while ensuring that glass vessel 50 is firmly kept onto the pump thanks to plastic housing 130 enclosing it, and that pusher 17 of the device can properly reach piston 51. In this manner, precise drug doses can be administered in controlled and reliable manner.

Referring to FIGS. 13a to 13f, a fourth embodiment of the invention will be described, essentially characterized in that there is provided a pair of wings, 271a, 271b, that can be hinged to the infusion pump and are capable of preventing a connection element 260, for instance of the kind having a piercing element 261 and known as "spike" within the field, from slipping out when said connection element is inserted in the glass vessel 50 housed within a housing 230.

A cartridge 220 comprises a housing 230 of plastic material having an open proximal end 231 and an open distal end 232 and consisting of a cylindrical base part 233 and a neck part 235. Base part 233 is substantially shaped as a cylindrical cup having a proximal end and a distal end. Neck part 235 is substantially shaped as an inverted funnel with a neck, and it has a proximal end and a distal end. The proximal end of base part 233 coincides with the proximal end of housing 230 itself. The distal end of neck part 235 coincides with the distal end of housing 230. When housing 230 is assembled, the distal end of base part 233 substantially matches the proximal end of neck part 235.

In order to enable the mutual fastening of base part 233 and neck part 235, snap fitting formations are provided, which are integrally formed on the inner and outer surface of said parts, respectively. In the example illustrated, the snap fitting formations include a pair of diametrically opposite teeth 236 formed on tabs 236a axially extending from neck part 235 of housing 230, and a pair of diametrically opposite seats or openings 237, which are formed on the side wall of neck part 235 of housing 230 and into which teeth 236 are inserted when housing 230 is assembled.

In order to make coupling between teeth 236 and seats 237 easier, the tabs provided with teeth 236 may be provided with draft end portions 236b with rounded or bevelled edges.

Tabs 236a are preferably located so that, when cartridge 220 is inserted onto pump 10, said tabs 236a are radially aligned with eyelets 16 provided on retaining projections 14, arranged in fork configuration, of pump 10. Moreover, base part 233 of housing 230 is suitably sized so that said tabs 236a are in contact with eyelets 16. In other words, eyelets 16 define an abutment shoulder for tabs 236a and consequently prevent outward radial movement thereof.

Advantageously, thanks to such an arrangement, eyelets 16 prevent tabs 236a from radially opening outwards, thereby avoiding the risk that neck part 235 becomes released from base part 233 of housing 230, especially when piston 17 of pump 10 exerts the pushing force on piston 51 of vessel 50. When cartridge 220 is inserted onto pump 10 with vessel 50 inside it, consequently neck part 235 cannot be removed from base part 233 thanks to the engagement of teeth 236 with seats 237 and thanks to the fact that tabs 236a provided with teeth 236 cannot open out outwards due to the provision of eyelets 16. Other configurations will be possible in which eyelets 16 are replaced by corresponding stop members for tabs 236a. For instance, said corresponding stop members could consist of projections integrally formed in retaining projections 14, or of heads of screws for fastening retaining projections 14.

Advantageously, each tab 236a can include two or more axially aligned teeth 236 and, on the side wall of neck part 235 of housing 230, there are formed as many seats or openings 237 into which teeth 236 are inserted when housing 230 is assembled. The two or more teeth 236 provided on each tab 236a can also have mutually different sizes, and preferably the teeth size decreases towards the draft end portion 236b.

Inside neck part 235 of housing 230, a substantially cylindrical cavity 239a is formed. At its distal end 232, neck part 235 has an opening 251 with smaller diameter than its proximal end 231.

Base part 233 of housing 230 is defined at its proximal end by an internal flange 238, integrally formed on base part 233 and located in correspondence of the tapered portion on which fitting formations 221 are formed. Internal flange 238 thus surrounds an opening 239b having a smaller diameter than internal cavity 239a of neck part 235.

Similarly to the previously described embodiments, cartridge 220 of which housing 230 is part further includes a glass vessel 50 containing a drug and enclosed inside housing 230.

Cartridge 220 further comprises a connection element 60 suitable for being arranged at distal end 50b of the vessel 50.

Proximal end 50a of vessel 50 is received within proximal end 231 of housing 230, together with the proximal end of neck part 235, with piston 51 being arranged coaxially with opening 239b formed on proximal end 231 of base part 233 of housing 230. The proper and quick alignment of piston 51 with opening 239b is ensured by axial ribs formed inside base part 233 of housing 230. Neck part 235 is so sized in length as to enclose the whole of the cylindrical portion of the vessel 50, or at least most of such portion.

Distal end 50b of vessel 50 is received within distal end 232 of housing 230.

Retention of vessel 50 inside housing 230 is ensured in that distal end 232 of neck part 235 has a tapered inner wall 232a forming a corresponding abutment surface and resting on the tapered portion of vessel 50, between the cylindrical portion and the neck thereof, thereby pushing vessel 50 against internal flange 238 of base part 233 of housing 230.

In the alternative, a small passageway can be provided between surface 232a and vessel 50, and vessel 50 can be retained in correspondence of base part 233, for instance through the mutual engagement between annular projection 50c provided at the base of vessel 50 and a corresponding annular seat 233a provided in base part 233.

According to this fourth embodiment of the invention, cartridge 220 comprises a housing 230 having a pair of wings 271a,271b, preferably made of plastic material, capable of assuming a closed configuration (FIG. 13c) and an open configuration (FIG. 13f). The open configuration allows axially inserting housing 230 on pump 10 and, more particularly, exploiting the bayonet coupling provided on pump 10, for inserting fitting formations 221 into the fork of socket 13 and, after the cartridge has been turned by 90° about its longitudinal axis, retaining it in slits 15 of retaining projections 14.

Advantageously, wings 271a,271b are provided, at a proximal end 273, with pairs of hinges 275 in which a hinge pin 277 inserted in eyelet 16 is engaged. In the illustrated embodiment, pins 277 are mutually parallel. Wings 271a, 271b comprise, at a distal end 279, a corresponding "L"-shaped portion 281 oriented inwardly, i.e. towards the vessel 50, when housing 230 is mounted on pump 10. When wings 271a,271b are in their closed configuration, portions 281 are mutually adjacent and close housing 230 frontally, thus preventing slipping out of connection element 260, for instance of the "spike" type, having a Luer Lock connection 63 for an infusion set, inserted in the front end of vessel 50, at a pierceable membrane 53 provided there for outflow of the content, typically a drug.

Wings 271a,271b are shaped so as to surround, at least partially, housing 230, leaving free the distal end for slipping out of connection element 63 on which the infusion set will be fitted for delivering the drug to the patient. To this aim, wings 271a,271b are provided with a front or distal half-opening 283, preferably having a semicircular shape, said half-openings defining a corresponding circular opening when the wings are closed by bringing them against housing 230 of the cartridge.

At least one of the distal portions 283 of wings 271a,271b is further provided with at least one projection 285 having a snap-fitting tooth capable of engaging into a corresponding seat in the portion 283 of the opposite wing 271a,271b. The mutual engagement between the tooth of projection 285 and the corresponding seat causes snap-closing of the two wings around housing 230. A push-button provided on the outer surface of at least one of the distal portions 283 of wings 271a,271b allows disengagement of the snap-closing of the wings for bringing the wings 271a,271b to the open configuration.

The assembly described above can be inserted onto pump 10, while ensuring that glass vessel 50 is firmly kept onto the pump 10 thanks to plastic housing 230 enclosing it, and that pusher 17 of the device can properly reach piston 51. In addition, wings 271a,271b, when closed against housing 230, advantageously prevent connection element 260 from being inadvertently taken out, for example if the cannula associated to fitting 63 were forcedly pulled.

In this manner, precise drug doses can be administered in controlled and reliable manner.

The invention as described and illustrated can be subject to several variants and modifications falling within the same inventive principle.

The invention claimed is:

1. A cartridge (120; 220) for an infusion pump (10) for controlled administration of drugs to a human or animal body, comprising:
    a housing (130; 230) and a glass vessel (50) of cylindrical shape, said glass vessel (50) having a cylindrical portion with an open proximal end (50a) closed by a slidable piston (51) and a distal end (50b) having an opening closed by a pierceable membrane (53) and provided with a neck, said housing (130; 230) enclosing said glass vessel (50),
    wherein said housing (130; 230) is made of plastic material and has an open proximal end (131; 231) and an open distal end (132; 232) adapted to receive the proximal end (50a) of the vessel (50) and the distal end (50b) of the vessel (50), respectively,
    wherein the open proximal end (131; 231) of the housing (130; 230) is provided with a pair of bayonet fitting formations (121; 221) integrally formed on the housing (130; 230) for fastening the cartridge (120, 220) to an infusion pump (10),
    wherein the housing (130; 230) includes a cylindrical base part (133; 233), which is provided with an inner flange (138; 238) for abutment of the vessel (50) and on which the fitting formations (121; 221) are formed, and a neck part (135; 235) that can be fastened to the base part (133; 233) by snap fitting formations (136, 137; 236, 237) for retaining the glass vessel (50) between the base part (133; 233) and the neck part (135; 235) of the housing (130; 230),
    wherein the inner flange (138; 238) provided for abutment of the vessel (50) inside the cylindrical base part (133; 233) surrounds an opening having a smaller diameter than an internal cavity of the neck part (135; 235);
    wherein the snap fitting formations (136, 137; 236, 237) are configured so as to make separation of the neck part (135; 235) from the base part (133; 233) difficult or substantially impossible, whereby the glass vessel (50) and the housing (130; 230) form a disposable assembly,
    wherein positions of the snap fitting formations (136, 137, 236, 237) on the housing (130; 230) are angularly aligned with positions of said bayonet fitting formations (121; 221) on the base part (133; 233),
    wherein the snap fitting formations (136; 236) include a pair of diametrically-opposed, axially-extending tabs (136a; 236a) on the base part (133; 233) on which a pair of inwardly-extending diametrically opposite teeth (136; 236) are located, and wherein the snap filling formations (137; 237) include a pair of diametrically opposite inwardly-extending recessed seats (137; 237) formed within a sidewall of said neck part (135; 235),
    wherein the neck part (135; 235) is sized in length so as to enclose a whole of the cylindrical portion of the vessel (50), and
    wherein retention of the vessel (50) within the housing (130; 230) is ensured by the distal end (132; 232) of the housing (130; 230) provided by the neck part (135, 235) having a tapered inner wall (132a; 232a) forming an abutment surface for an upper tapered portion of the vessel (50) extending between the cylindrical portion and the neck of the vessel (50), thereby urging the vessel (50) against the inner flange (138; 238) of the base part (133; 233) of the housing (130; 230).

2. The cartridge according to claim 1, further comprising a connection element (260) arranged at the distal end (50b) of the vessel (50) for fluidically connecting an inside of the vessel (50) to an infusion set, and further comprising an infusion pump (10) connected to the cartridge, wherein said housing comprises a pair of wings (271a, 271b) that can be hinged to the infusion pump and are capable of preventing the connection element (260) from slipping out when inserted in the glass vessel (50) housed within the housing (230), said wings (271a, 271b) comprising, at a distal end (279), a corresponding "L"-shaped portion (281) oriented inwardly, towards the vessel (50), when the housing (230) is mounted on the pump (10), whereby, when the wings (271a, 271b) are in their closed configuration, said "L"-shaped portions (281) are mutually adjacent and close the housing (230) frontally, thus preventing slipping out of said connection element (260) inserted in a front end of the vessel (50), at the pierceable membrane (53) provided therein for outflow of a drug.

3. The cartridge according to claim 1, wherein the neck part of the housing has an opening sized so as to enable a connection element, arranged at the distal end of the vessel, to outwardly protrude for fluidically connecting an inside of the vessel to an infusion set.

4. The cartridge according to claim 1, further comprising a connection element (260) adapted to be arranged at the distal end of the vessel for fluidically connecting an inside of the vessel to an infusion set.

5. The cartridge according to claim 4, wherein the connection element (260) comprises at a proximal end a piercing element (261) for piercing the membrane of the vessel, and at a distal end a fitting (63) for connection to an infusion set.

6. The cartridge according to claim 1, wherein the vessel (50) is retained in correspondence of the base part (233) via mutual engagement between an annular projection (50c) provided at a base of the vessel (50) and a corresponding annular seat (233a) provided in the base part (233).

7. The cartridge according to claim 1, wherein an inner diameter of the cylindrical portion of the glass vessel (50) is substantially equal to a diameter of the opening surrounded by the inner flange (138; 238) of the base part (133; 233) of the housing (130; 230).

8. A cartridge (220) for an infusion pump (10) for controlled administration of drugs to a human or animal body, comprising:

a housing (230) and a glass vessel (50) of cylindrical shape, said glass vessel (50) having a cylindrical portion with an open proximal end (50a) closed by a slidable piston (51) and a distal end (50b) having an opening closed by a pierceable membrane (53) and provided with a neck, said housing (230) enclosing said glass vessel (50);

wherein said housing (230) is made of plastic material and has an open proximal end (231) and an open distal end (232) adapted to receive the proximal end (50a) of the vessel (50) and the distal end (50b) of the vessel (50), respectively;

wherein the open proximal end (231) of the housing (230) is provided with a pair of bayonet fitting formations (221) integrally formed on the housing (230) for fastening the cartridge (220) to an infusion pump (10);

wherein the housing (230) includes a cylindrical base part (233), which is provided with an inner flange (238) for abutment of the vessel (50) and on which the fitting formations (221) are formed, and a neck part (235) that can be fastened to the base part (233) by snap fitting formations (236, 237) for retaining the glass vessel (50) between the base part (233) and the neck part (235) of the housing (230);

wherein the inner flange (238) provided for abutment of the vessel (50) inside the cylindrical base part (233) surrounds an opening having a smaller diameter than an internal cavity of the neck part (235);

wherein the snap fitting formations (236, 237) are configured so as to make separation of the neck part (235) from the base part (233) difficult or substantially impossible, whereby the glass vessel (50) and the housing (230) form a disposable assembly;

wherein positions of the snap fitting formations (236, 237) on the housing (230) are angularly aligned with positions of said bayonet fitting formations (221) on the base part (233), wherein the snap fitting formations (136; 236) include a pair of diametrically-opposed, axially-extending tabs (136a; 236a) on the base part (133; 233) on which a pair of inwardly-extending diametrically opposite teeth (136; 236) are located, and wherein the snap filling formations (137; 237) include a pair of diametrically opposite inwardly-extending recessed seats (137; 237) formed within a sidewall of said neck part (135; 235), wherein the neck part (235) is sized in length so as to enclose a whole of the cylindrical portion of the vessel (50); and wherein the vessel (50) is retained in correspondence of the base part (233) via mutual engagement between an annular projection (50c) provided at a base of the vessel (50) and a corresponding annular seat (233a) provided in the base part (233) of the housing (230).

9. The cartridge according to claim 8, further comprising a connection element (260) arranged at the distal end (50b) of the vessel (50) for fluidically connecting an inside of the vessel (50) to an infusion set, and further comprising an infusion pump (10) connected to the cartridge, wherein said housing comprises a pair of wings (271a, 271b) that can be hinged to the infusion pump and are capable of preventing the connection element (260) from slipping out when inserted in the glass vessel (50) housed within the housing (230), said wings (271a, 271b) comprising, at a distal end (279), a corresponding "L"-shaped portion (281) oriented inwardly, towards the vessel (50), when the housing (230) is mounted on the pump (10), whereby, when the wings (271a, 271b) are in their closed configuration, said "L"-shaped portions (281) are mutually adjacent and close the housing (230) frontally, thus preventing slipping out of said connection element (260) inserted in a front end of the vessel (50), at the pierceable membrane (53) provided therein for outflow of a drug.

10. The cartridge according to claim 8, wherein the neck part of the housing has an opening sized so as to enable a connection element, arranged at the distal end of the vessel, to outwardly protrude for fluidically connecting an inside of the vessel to an infusion set.

11. The cartridge according to claim 8, further comprising a connection element (260) adapted to be arranged at the distal end of the vessel for fluidically connecting an inside of the vessel to an infusion set.

12. The cartridge according to claim 11, wherein the connection element (260) comprises at a proximal end a piercing element (261) for piercing the membrane of the vessel, and at a distal end a fitting (63) for connection to an infusion set.

13. The cartridge according to claim 11, wherein the distal end (232) of the housing (230) provided by the neck part (235) has a tapered inner wall (232a) adjacent and spaced from an upper tapered portion of the vessel (50) extending between the cylindrical portion and the neck of the vessel (50) such that a passageway is provided by the spacing between the tapered inner wall (232a) and the upper tapered portion of the vessel (50).

14. The cartridge according to claim 8, wherein an inner diameter of the cylindrical portion of the glass vessel (50) is substantially equal to a diameter of the opening surrounded by the inner flange (238) of the base part (233) of the housing (230).

* * * * *